United States Patent [19]

Kiesel et al.

[11] Patent Number: 4,657,217
[45] Date of Patent: Apr. 14, 1987

[54] PARALLELOGRAM BRACKET ASSEMBLY WITH A FORCE BALANCING MECHANISM

[75] Inventors: Helmut Kiesel; Klaus Stoeckl, both of Bensheim, Fed. Rep. of Germany

[73] Assignee: Siemens Aktiengesellschaft, Berlin and Munich, Fed. Rep. of Germany

[21] Appl. No.: 806,830

[22] Filed: Dec. 10, 1985

[30] Foreign Application Priority Data

Dec. 10, 1984 [DE] Fed. Rep. of Germany ....... 3445016

[51] Int. Cl.$^4$ .............................................. E04G 3/00
[52] U.S. Cl. ............................... 248/280.1; 248/281.1
[58] Field of Search ............... 248/280.1, 281.1, 123.1, 248/655, 665, 324, 325, 292.1; 433/79

[56] References Cited

U.S. PATENT DOCUMENTS

| 4,080,530 | 3/1978 | Krogsrud ..................... 248/280.1 X |
| 4,160,536 | 7/1979 | Krogsrud ......................... 248/280.1 |
| 4,166,602 | 9/1979 | Nilsen et al. . |
| 4,397,439 | 8/1983 | Wilbur ......................... 248/281.1 X |
| 4,427,382 | 1/1984 | Hoffmeister et al. . |

FOREIGN PATENT DOCUMENTS 724471 2/1955 United Kingdom .
1056379 1/1967 United Kingdom .

Primary Examiner—J. Franklin Foss

[57] ABSTRACT

A parallelogram bracket assembly with a force balance mechanism which utilizes a pneumatic spring situated in the parallelogram bracket assembly. The pneumatic spring has a cylinder receiving a piston which has a piston rod and the cylinder is supported against parts connected to one articulated axle and an end of the piston rod is supported against parts which are connected to an articulated axle diametrically arranged to the one articulated axle. According to the invention, one of the rod members forming the parallelogram bracket assembly has a tubular guide channel for the telescopic acceptance of the pneumatic spring in a manner to allow an easy interchangeable fashion. For easy replacement of the pneumatic spring, an end piece is connected to the articulated axle and is releasably held at least at one end of the guide channel and the piston rod or the cylinder presses against this end piece.

17 Claims, 13 Drawing Figures

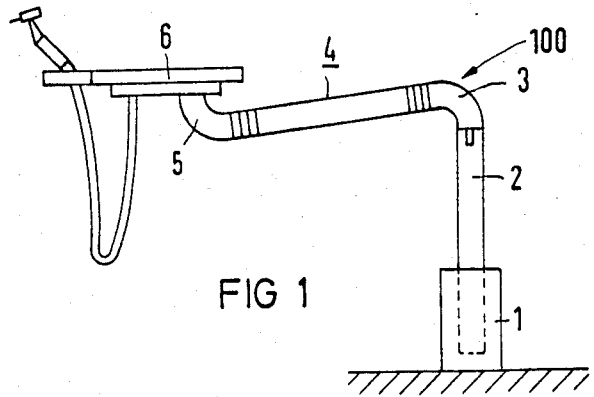
FIG 1
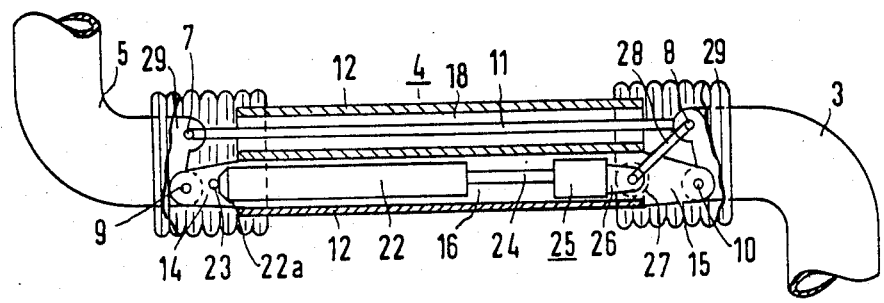
FIG 2
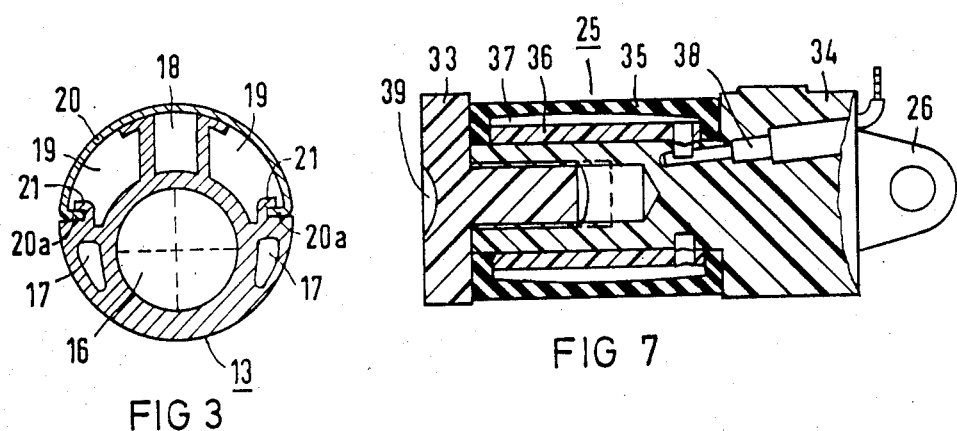
FIG 3
FIG 7

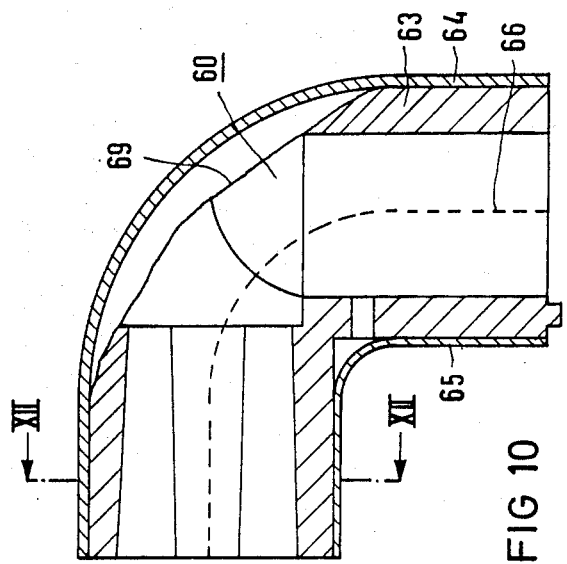
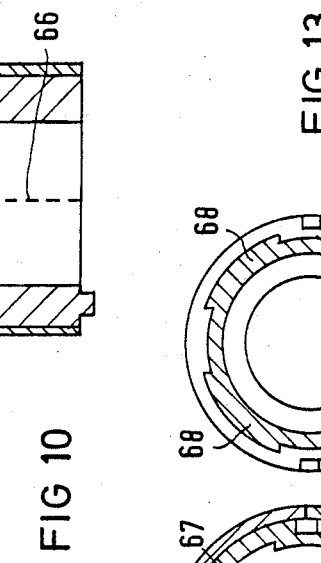
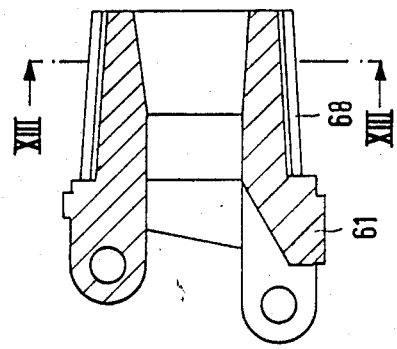
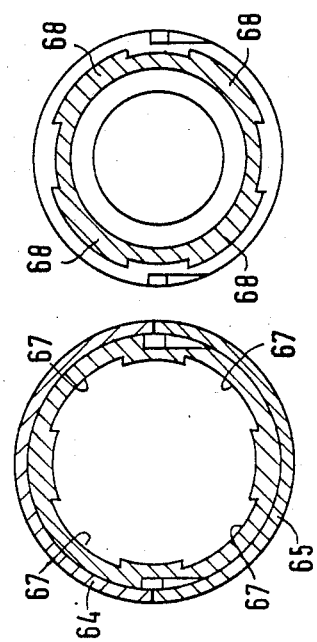
FIG 10
FIG 11
FIG 12
FIG 13

PARALLELOGRAM BRACKET ASSEMBLY WITH A FORCE BALANCING MECHANISM

BACKGROUND OF THE INVENTION

The present invention relates to a parallelogram bracket which has a pair of rod members pivotally connected to end members and has a force balancing mechanism which utilizes a pneumatic spring situated in the parallelogram bracket. A piston of the pneumatic spring is supported against parts which are connected to one of the articulated axles and the piston rod is supported against parts of the parallelogram rod member connected to the other articulated axle situated diagonally opposite thereto.

A known parallelogram bracket, which is disclosed in U.S. Pat. No. 4,166,602, is provided for holding an x-ray unit and has a pneumatic spring which is situated in a hollow cast member forming one of the arm members of the parallelogram. The pneumatic spring includes a cylinder containing a piston which is connected to a piston rod which cylinder and piston rod are each provided with an end piece of which one is linked to a yoke applied to the cast member and the other is linked to a lug interacting with an adjustment screw. The point of attachment for the piston rod can be changed with the adjustment screw and thus the moment of force can be modified and thus adapted to loads of different weights. The end pieces are connected to the piston rod and respectively to the cylinder by means of screw-type connections so that the ends of the cylinder and piston rods must be mated to the end pieces and thus the structure of the parallelogram bracket.

Even though the mechanical outlay can be clearly reduced in comparison to traditional bracket structures working with compression springs, chains and cam elements by employing a pneumatic spring, the known bracket structure is nonetheless relatively complicated particularly in view of the assembly and disassembly of the pneumatic spring as well as the use of the bracket for carrying other objects with loads of different weights lying outside of the range of the adjustment of the adjusting screw. To compensate for loads having a weight outside of the range for the bracket structure, the structure must be disassembled because the range of weight compensation for loads of this structure is essentially a relatively narrow range.

SUMMARY OF THE INVENTION

The present invention is to provide a bracket structure which is improved in comparison to the known structure and is even a simpler and more cost-saving bracket structure which allows one and the same bracket to be utilized for carrying different objects having weight loads of different sizes without modifying the structure and which also enables brackets differing in length to be provided for different uses and load arrangements upon employment of as many identical parts as possible.

To accomplish these goals, the present invention is directed to an improvement in a parallelogram bracket assembly with a force balance mechanism which utilizes a pneumatic spring situated in the parallelogram bracket, the parallelogram bracket is composed of a pair of parallel arm members, which are connected to yokes as end members by pivotal connection to form a parallelogram arrangement, said pneumatic spring having a cylinder and a piston rod and extending between a pivotal connection of one rod member to one yoke and the pivotal connection of the other rod member to the other yoke which connections are diametrically opposite each other. The improvements comprises one of the arm members having a tubular guide channel with the pneumatic spring being inserted in the guide channel in an easily interchangeable fashion and being closed at one end by an end piece releasably held at one end of the guide channel.

In that there is no rigid connection adapted to the specific bracket structure between the pneumatic spring and the end pieces of the parallelogram arms, the pneumatic spring can be very easily changed and under given conditions can be replaced by other pneumatic springs having a different filling pressure so that the bracket of identical lengths can be utilized for loads of different sizes. Depending upon the particular use, only a pneumatic spring remaining identical in terms of its dimensions need be changed without having to modify the bracket structure. This is easily possible on the basis of the bracket structure described in greater detail hereinbelow. Under given conditions, a replacement can even be undertaken by the customer himself, this being particularly significant for use of brackets in countries not having a good service network.

The pneumatic spring is advantageously situated in a circumferentially closed guide channel of a profile member and is therefore not visible from the outside.

Further advantages and objects of the improved structure will be readily apparent from the following description and drawings of an exemplary embodiment of the invention which are set forth hereinbelow.

BRIEF DESCRIPTION OF THE DRAWINGS

FIG. 1 is a schematic illustration of a bracket structure utilizing the parallelogram bracket assembly in accordance with the present invention;

FIG. 2 is a longitudinal cross-sectional view with portions in elevation of a parallelogram bracket assembly in accordance with the present invention utilized in the device of FIG. 1;

FIG. 3 is a cross-sectional view of a profile member utilized in forming the bracket assembly of FIG. 2;

FIG. 7 is an enlarged cross-sectional view of a braking means or device for the bracket assembly of FIG. 2;

FIG. 10 is a transverse cross-sectional view of an elbow part forming each elbow of FIG. 1;

FIG. 11 is a cross-sectional view of an end piece for the elbow of FIG. 1;

FIG. 12 is a cross-sectional view taken along lines XII—XII of FIG. 10; and

FIG. 13 is a cross-sectional view taken along lines XIII—XIII of FIG. 11.

DESCRIPTION OF THE PREFERRED EMBODIMENTS

Figure 6:
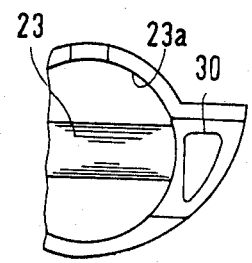
FIG. 6 is a partial end view of the end piece of FIG. 4.

The principles of the present invention are particularly useful in a parallelogram bracket assembly or structure 4 which is utilized in the dental field. An example of the use of the bracket assembly 4 is illustrated in FIG. 1 wherein an adjustable instrument support device 100 is illustrated. The support device 100 has a vertically extending support pipe 2, which is secured in a pedestal or base part 1 which is illustrated as being fastened to the floor. The support pipe 2 terminates in a elbow 3 which has an opposite end connected to the parallelogram bracket assembly 4 which extends between the elbow 3 and a second elbow 5. The other end of the second elbow 5 supports a dental instrument table 6. The instrument table 6 can be adjusted in height through a certain range with the parallelogram bracket assembly 4 in a known manner. Instead of an instrument table, some other device, for example, an x-ray apparatus or a light can also be held by the device 100 of FIG. 1. It is also possible that instead of mounting the device 100 of FIG. 1 on the floor as illustrated, the pedestal 1 is secured to the ceiling so that the vertical pipe 2 is mounted on the ceiling to provide a ceiling suspension for the device.

The structure of the parallelogram bracket assembly 4 is shown in greater detail in FIG. 2. The parallelogram bracket assembly 4 is formed by a first horizontally extending rod member 11 which is connected at one end by a first articulated axle 7 to a member or yoke 29 of the elbow 5 and at the other end by a second articulated axle 8 to a member yoke 29 of the elbow 3. A second arm member 12, which is formed by a tubular member has one end connected to the yoke 29 of elbow 5 by a third articulated axle 9 and to the member 29 of the elbow 3 by a fourth articulated axle 10. The yokes 29 and two arms 11 and 12 form a parallelogram arrangement with each of the axles 7-10 being a part of a pivotal connection. The member 12 is formed by a tubular profile member 13 (FIG. 3) which has end pieces 14 and 15 joined to it to form the connections of the third and fourth articulated axles 9 and 10.

As best illustrated in FIG. 3, the profile member 13 has a plurality of longitudinally extending guide channels 16 through 19 in which some are partially closed and some are partially opened toward the periphery of the member 13. Specifically, there is a centrally placed guide channel 16 which has a circular cross-section, two laterally closed guide channels 17 which have roughly a triangular cross-section and are situated symmetrically to the channel 16. A guide channel 18 opens towards the top and is positioned above the guide channel 16 and then there are two upper lateral guide channels 19 which are situated on each side of the central upper guide channel 18 and these channels 19 are also open on their periphery. The profile member 13 has two longitudinally extending projections to form longitudinal grooves 21 and the periphery of the channels 18 and 19 are closed by a cover or cap member 20 which has inturned edges 20a gripped in the grooves 21.

As illustrated in FIG. 2, the first rod member 11 is received in the upper guide channel 18. The two outer guide channels 19 serve for the guidance of various electrical, pneumatic and/or hydraulic supply lines which are to be conducted from a connection box in the base part or pedestal 1 to the user such as handpieces supported on the instrument table 6. When the cap or sleeve 20 is removed, the lines can be laid within the channels 19 of the profile member 13 in a particularly easy fashion or, respectively, can be replaced as needed. For the purpose of conducting the lines within the elbows 3 and 5, as shall be seen in greater detail hereinbelow, also are provided with removable caps or sleeves which guarantee good access to the lines after the caps or sleeves are removed. As can be seen from FIG. 3, the cap or sleeve 20 together with the profile member 13 forms a circular outside contour with the cap or sleeve 20 covering roughly half of the circumference of the profile member. An extruded profile is advantageously utilized as the profile member 13 and the cap can be expediently composed of plastic.

A pneumatic spring 22 is placed in the peripherally closed guide channel 16 (FIG. 2). One end 22a which is illustrated as being an end of the cylinder of the spring 22 is supported against a cross-bolt or pin 23 of the end piece 14 and the pin 23 forms a force transmission member and extends across an opening or channel 23a of the end piece 14. The free end of a piston rod 24 bears against one end face of a second force transmission member 25 which is a braking member and is illustrated in greater detail hereinafter. The member 25 has a projection 26 which on the one hand supports a guide roller 27 and on the other hand is pivotally connected to a rod joint 28 that extends to the second articulated axle 8. Thus, the member 25 is connected for pivotal movement both to the member 28 and also about the second articulated axle 8. In addition, the member 25 moves axially in the guide channel 16.

Disassembly of the pneumatic spring, for instance, in order to replace it with one having a higher gas pressure to support loads with higher weight, can be easily executed. After releasing the axle 9, the bracket 4 and the elbow 5 can be pivoted relative to each other around the first axle 7. Then, the cross-bolt or force transmission member 23 is removed and the pneumatic spring can be taken out through the longitudinally extending channel or opening 23a which is illustrated in FIG. 5.

Each of the articulated axles between the parallelogram rod members and the two elbows 3 and 5 are covered by a concertina bellows such as 29.

Figure 4:
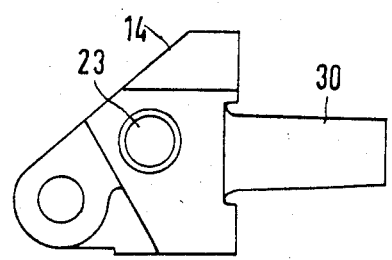
FIG. 4 is a side view of one end piece of the bracket assembly of FIG. 2.
Figure 5:
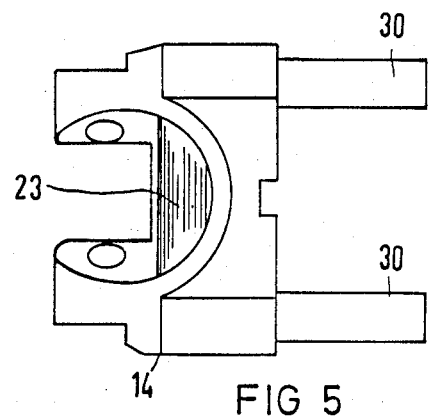
FIG. 5 is a plan view of the end piece of FIG. 4.

As best shown in FIGS. 4 through 6, the end piece 14, which is also identical to the end piece 15, has centering prongs or projections 30 on both sides which correspond in cross-section to the cross-section of the guide channels 17 of the profile member 13. After insertion of the prongs in the channel 17, they can be firmly connected to the tubular profile member 13 in a suitable fashion such as by applying glue or an adhesive.

Alternatively, it is also conceivable to not firmly connect the end piece 14 to the profile member 13 but on the contrary only to plug the prongs 30 into the guide channel 17. This provides an alternate way of interchanging the pneumatic spring which is different than the above-described method. Instead of removing the bolt 23, the entire end piece can be removed from the profile member 13 and then the spring 22 is replaced.

The structure of the braking device is best illustrated in FIG. 7. The braking device 25 is essentially composed of two plastic parts 33 and 34 which are threaded or screwed to one another and have a rubber-elastic brake element 35 which is placed in an annular recess formed by different outer diameters of the plastic parts 33 and 34. An annular plastic part 36 is interposed concentrically to the elastic element 35 to help grip the element with the members 33 and 34 and to form an annular pressure chamber 37 between the member 36 and element 35. The pressure chamber 37 is in communication with a compressed air source through a conduit such as 38. At its end face, the plastic part 33 has a notch or recess 39 in which the end of the piston rod 24 can be supported.

The braking device or means 25 serves the purpose of enabling locking the bracket assembly in a desired position given a load of an additional weight, for example, given devices such as a film viewer, plaque-removing device, etc., temporarily being placed on the instrument table 6. To this end, a valve for releasing compressed air from a compressed air source to the chamber 37 can be expediently provided in the proximity of the instrument table 6. When charged with compressed air, the generated surface of the elastic element 35, which in the unextended condition has a diameter which is slightly less than the outer diameters of the plastic parts 33 and 34, is placed or expanded against the wall of the tubular channel 16. In this position, the part 25 is locked in position and any dislocation or adjustment of the bracket assembly is no longer possible.

Figure 8:
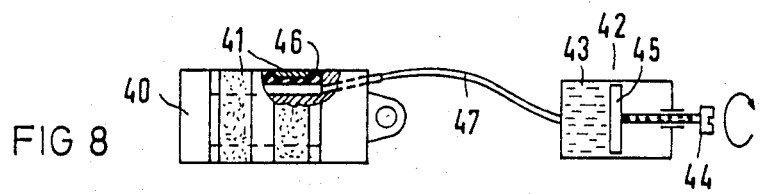
FIG. 8 is a modification of a braking device with portions broken away for purposes of illustration.
Figure 9:
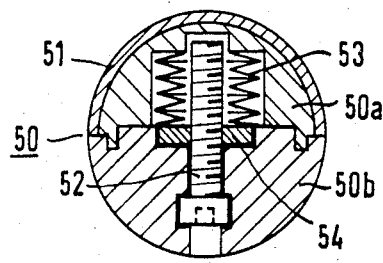
FIG. 9 is a cross-sectional view of another modification of a braking device or means.

For cases in which an intentional dislocation is appropriate, one or more frictional elements, whose frictional force is adjustably variable if need be to define values, can be provided instead of the braking element 25 or in addition thereto. The adjustments can therefore occur mechanically, pneuamtically or hydraulically. Three alternatives are schematically shown in FIGS. 8 and 9. In the alternative or modification of FIG. 8, a braking device 40 is constructed similar to the device 25 of FIG. 7. In addition to the rubber-elastic brake element 35 of the device of FIG. 7, a plurality of friction elements 41 situated on a circumference whose frictional force relative to the tubular wall can be hydraulically set are provided. A hydraulic adjustment means 42 can set the frictional force of the brake element 41 and is provided externally of the bracket assembly preferably in the proximity of an instrument table 6. The adjustment means 42 is composed of a cylinder 43 filled with a suitable fluid and a piston 45 which is manually adjusted by means of an adjustment screw 44. The adjustment means 42 is connected by a line 47 to a chamber 46 of the brake means 40. The hydraulic fluid can be set to the pressure necessary for adjusting the frictional force by changing the position of the piston 45 by means of the adjustment screw 44.

A mechanical adjustment of the frictional force can also be provided instead of the hydraulic adjustment. An example is illustrated in FIG. 9 wherein a braking device 50 is composed of two half shells 50a and 50b of which the first has a friction lining 51. Instead of having a single lining 51, a plurality of friction elements could be mounted on the member 50a. The half shell 50a is pressed against the wall of the channel 16 in its mounted condition by means of an adjustment member situated in the other half shell 50b. The adjustment member is illustrated as having the form of a hexagonal screw 52 guided in a threaded nut 54 with a plurality of resilient elements such as saucer springs 53 interposed between the nut 54 and a bearing surface of the member 50a. Such a mechanical adjustment of friction force is appropriate when the weight or load attacking the bracket is largely fixed but an adjustment of the bracket given the provided load should be set with an individual tightness.

Instead of the externally blockable pneumatic spring, pneumatic springs having controllable valves situated in an integrated fashion can also be provided with these being triggered upon actuation of the piston rod. It is advantageous given employment of such a pneumatic spring to provide a pneumatic control means in order to be able to control the trip tappets of the pneumatic spring for release or, respectively, blocking the gas exchange within the chamber in the pneumatic spring.

The structure of the elbow 3 or 5 is best illustrated in FIGS. 10 through 13. Both elbows are constructed by using identical component parts that are composed of a pipe bend 60 and a link head 61 which is secured in the end of the pipe bend. The pipe bend 60 is in turn composed of cast members 63 and two half shell coverings or sleeve members 64 and 65, which are held on the cast member 63 in a removable fashion, are connected to one another at a parting line 66 in a suitable way, for example, by means of resilient catch elements. This particular construction has a number of advantages in that the outer visible parts of the bend are formed by two plastic half shells and the surface of the cast member need not be reworked or further finished. In particular, relatively involved grinding, coating and lacquering work is eliminated. Requests for different colors may be taken into consideration when producing the plastic half shells so that merely changing the half shell enables changing the color of the particular elbow.

At its end facing the bracket assembly, the cast member 53 has a socket with a cross-section shown in FIG. 12. As it may be seen, the comprises four grooves 67 uniformly distributed over the circumference with a conical taper towards the bend into which corresponding longitudinally proceeding ribs 68 of the link head 61 are received. As illustrated, the link head has the bearing surfaces for receiving articulating axles such as 8 and 10 of FIG. 2 and thus form a yoke member for connecting two of the rod members at one end.

The pipe end 60 can now be put in place on the link head 61 either as shown in FIG. 10 with its pipe end pointed down or displaced by 180°, i.e., with its pipe end directed upwardly. After the parts have been joined, they can be durably connected to one another in a suitable way, for example, by gluing, pinning or any other desirable method.

In the region of the bend, the cast member 63 contains an opening or aperture 69 which is covered by the half shell 64 when it is assembled on the cast member. After the half shell 64 has been removed, access to the inside of the bend from the outside is established so that, for example, lines laid within the supporting pipe arrangement 1 through 5 can easily be replaced.

Although various minor modifications may be suggested by those versed in the art, it should be understood that we wish to embody within the scope of the patent granted hereon, all such modifications as reasonably and properly come within the scope of our contribution to the art.

We claim:

1. A parallelogram bracket assembly comprising a pair of parallelly extending arms, said arms being connected at their ends to transverse members by pivotal connections to form a parallelogram arrangement, one of the two parallel arms having a tubular guide channel closed at each end by an end piece, a first member being connectd to one of the end pieces, a second member being received in the guide channel, a third member connecting the second member to the pivotal connection of the adjacent arm adjacent the other of said end pieces, a pneumatic spring having a piston and cylinder being inserted in said guide channel between said first and second members to press thereagainst so that the pneumatic spring applies a force between diametrically opposed pivotal connections of the assembly, and at least one of the two end pieces being constructed to allow easy removal of the pneumatic spring from said tubular guide channel.

2. A parallelogram bracket assembly according to claim 1, wherein pneumatic springs identical in terms of outside dimensions but variable in terms of filling pressure are employed for the force balance of loads of different weights.

3. A parallelogram bracket assembly according to claim 1, wherein each of the first and second members has means for releasably mounting the member in said tubular guide channel.

4. In a parallelogram bracket assembly having a force balancing mechanism including a pneumatic spring received in the bracket assembly, said bracket assembly having a pair of rod members extending parallel and being connected by pivotal connections at each end to a pair of yokes to form a parallelogram arrangement, said pneumatic spring having a cylinder containing a piston with a piston rod and being arranged to act between a pivotal connection of one of the pair of rod members and one of the pairs of yokes and a pivotal connection of the other of the pair of rod members to the other yoke of the pair of yokes so that the pivotal connections are diagonally opposite each other, the improvements comprising a first of the pair of rod members having a tubular guide channel, said pneumatic spring being inserted in said tubular guide channel in an easily interchangeable fashion, said guide channel at least at one end including an end piece connected to the respective pivotal connection and including a first force transmission member, said guide channel at an opposite end receives a second force transmission member, a rod element extending from said second transmission member to the pivotable connection of the other rod member to the yoke, each of the force transmission members having means for releasably mounting the member in said tubular guide channel, the second force transmission member having braking means for controllably securing the second member in a fixed axial position in the tubular channel, said free end of the piston rod being supported against said braking means, and the cylinder of the pneumatic spring engaging the first force transmission member in a releasable manner so that removal of the pneumatic spring through said one end is easily obtained.

5. In a parallelogram bracket assembly according to claim 4, wherein the one rod member is formed of a tubular profile having a plurality of longitudinal channels, said tubular profile having an end piece at each end for forming a pivotal connection with each yoke and the other rod member of the pair of rod members being received in one of the other longitudinally extending channels of the profile.

6. In a parallelogram bracket assembly according to claim 5, wherein the profile member is fashioned with channels open at their periphery forming longitudinally extending slots and the one member includes a cover and means for securing the cover on the profile member to cover said slots.

7. In a parallelogram bracket assembly according to claim 6, wherein the means for securing the cover comprise longitudinally extending grooves frictionally receiving edges of said cover.

8. In a parallelogram bracket assembly according to claim 6, wherein the profile member and cover form a cylindrical outside contour and the open channels of the profile are situated in approximately half the circumference of said profile member.

9. In a parallelogram bracket assembly according to claim 5, wherein the profile member contains the tubular guide channel which receives the pneumatic spring, second guide channels situated symmetrically to the first guide channel for receiving centering prongs of the end pieces for holding the end pieces engaged on said profile member and at least a third guide channel situated in line with the first guide channel for receiving the other rod member.

10. In a parallelogram bracket assembly according to claim 4, wherein the brake device contains one or more frictional elements and adjustable means for urging the frictional elements against an inner surface of the guide channel to lock the brake means in a given axial position.

11. In a parallelogram bracket assembly according to claim 10, wherein the adjustment means for urging includes an elastic brake element having a rubber-elastic formed part surrounding a chamber, and means for introducing a fluid into said chamber to radially expand said elastic member.

12. In a parallelogram bracket assembly according to claim 10, wherein the adjustable means comprise said brake member being composed of two half shell members adjusted relative to one another, at least one of said members having a frictional sleeve on an outer surface and means for urging the two members radially apart.

13. In a parallelogram bracket assembly according to claim 10, wherein the adjustable means for urging comprise a chamber receiving hydraulic fluid, and an externally positioned mechanical adjusting means for exerting hydraulic pressure in said chamber.

14. In a parallelogram bracket assembly having a force balancing mechanism including a pneumatic spring received in the bracket assembly, said bracket assembly having a pair of rod members extending parallel and being connected by pivotal connections at each end to a pair of yokes to form a parallelogram arrangement, said pneumatic spring having a cylinder containing a piston with a piston rod and being arranged to act between a pivotal connection of one of the pair of rod members and one of the pairs of yokes and a pivotal connection of the other of the pair of rod members to the other yoke of the pair of yokes so that the pivotal connections are diagonally opposite each other, the improvements comprising a first of the pair of rod members having a tubular guide channel and the pneumatic spring being inserted in said tubular guide channel in an easily interchangeable fashion, said guide channel at least at one end including an end piece connected to the respective pivotal connection and being engaged by one of the cylinder and piston rods in a releasable manner so that removal of the pneumatic spring through said one end is easily obtained, and each of the yokes being part of a link head of an elbow, said link head having a plug with a symmerical outside profile, said elbow having a pipe bend with a socket with an inside profile accepting and mating with the outside profile of the link head. head.

15. In a parallelogram bracket assembly according to claim 14, wherein the profiles of the link head and pipe bend comprise divisions which enable said link head to be inserted into said pipe bend in at least two positions offset by 180°.

16. In a parallelogram bracket assembly according to claim 15, wherein said pipe bend has an opening in the region of the bend which is accessible through a removable cover.

17. In a parallelogram bracket assembly according to claim 16, wherein said pipe bend is composed of a cast member and two half shell cover elements generating the outside surface of said pipe shell with at least the half shell covering said opening being situated on the cast member in an easily removable fashion.

* * * * *